US00PP17223P3

(12) United States Plant Patent
Giumarra et al.

(10) Patent No.: US PP17,223 P3
(45) Date of Patent: Nov. 21, 2006

(54) GRAPE PLANT NAMED 'ARRAONE'

(50) Latin Name: ***Vitis* sp.**
Varietal Denomination: Arraone

(75) Inventors: Salvador Giumarra, Edison, CA (US); Shachar Karniel, Edison, CA (US)

(73) Assignee: Agricultural Research & Development LLC, Edison, CA (US)

( * ) Notice: Subject to any disclaimer, the term of this patent is extended or adjusted under 35 U.S.C. 154(b) by 0 days.

(21) Appl. No.: 11/028,716

(22) Filed: Jan. 3, 2005

(65) Prior Publication Data

US 2006/0150289 P1 Jul. 6, 2006

(51) Int. Cl.
*A01H 5/00* (2006.01)

(52) U.S. Cl. ..... Plt./207

(58) Field of Classification Search ..... Plt./207
See application file for complete search history.

*Primary Examiner*—Kent Bell
*Assistant Examiner*—June Hwu
(74) *Attorney, Agent, or Firm*—Christie, Parker & Hale, LLP

(57) ABSTRACT

A new and distinct variety of Grapevine, designated 'Arraone', characterized by high crop yield, large bunches constantly produced, very uniform and attractive berries and bunches, and large, firm berries with bright white color.

2 Drawing Sheets

Botanical classification/cultivar denomination: *Vitis* sp. cultivar Arraone.

BACKGROUND OF THE INVENTION

The present invention relates to a new and distinct variety of Grapevine, botanically known as *Vitis* sp., and hereinafter referred to by the name 'Arraone'.

SUMMARY OF THE INVENTION

'Arraone' was bred by embryo rescue from the cross V 25/3×FL R47/63-229. It was asexually reproduced in Salinas, Calif., by tissue culture, emasculating seedless mother pollened with seedless father, and the seed trace rescued in tissue culture process. Observations made on 'Arraone' since May 1997 have shown that the unique features of this new Grapevine are stable and reproduced true to type in successive generations.

The new variety differs from other cultivars known to the inventor, including its parents, in the following traits, which have been repeatedly observed and are determined to be the unique and stable characteristics of 'Arraone':

1. Strong variety, producing high crop and large bunches constantly;
2. Berries and bunches are very uniform and attractive;
3. Berry size is large, bright white color; grapes are very firm;
4. Time of ripening is the last week of August and the general harvest time is the beginning of September;
5. Holds very well in cold storage and transportation.

These characteristics in combination distinguish 'Arraone' as a new and distinct Grapevine cultivar. All observations were made from four year old specimens grown in Bakersfield, Calif., from April to September 2003.

BRIEF DESCRIPTION OF ILLUSTRATIONS

The accompanying photographic illustrations show typical specimens of vegetative growth of four year old specimens of the new variety, in color as nearly true as it is reasonably possible to make in a color illustration of this character. Colors in the photograph may differ from the color values cited in the detailed botanical description below, which accurately describes the colors of the new Grapevine.

DESCRIPTION OF THE NEW VARIETY

Figure 1:
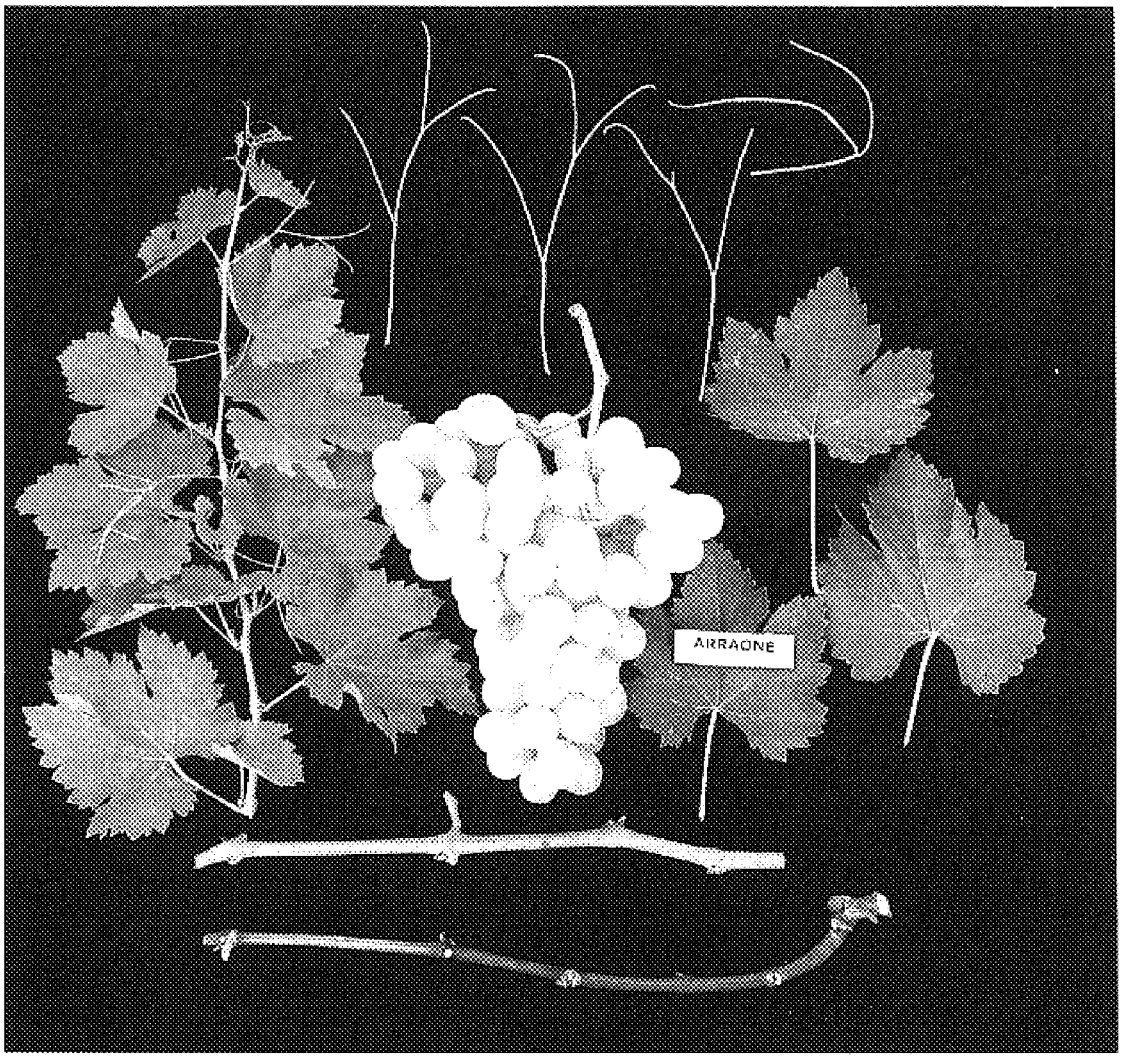
FIG. 1 shows leaves, stems and grapes of 'Arraone'.
Figure 2:
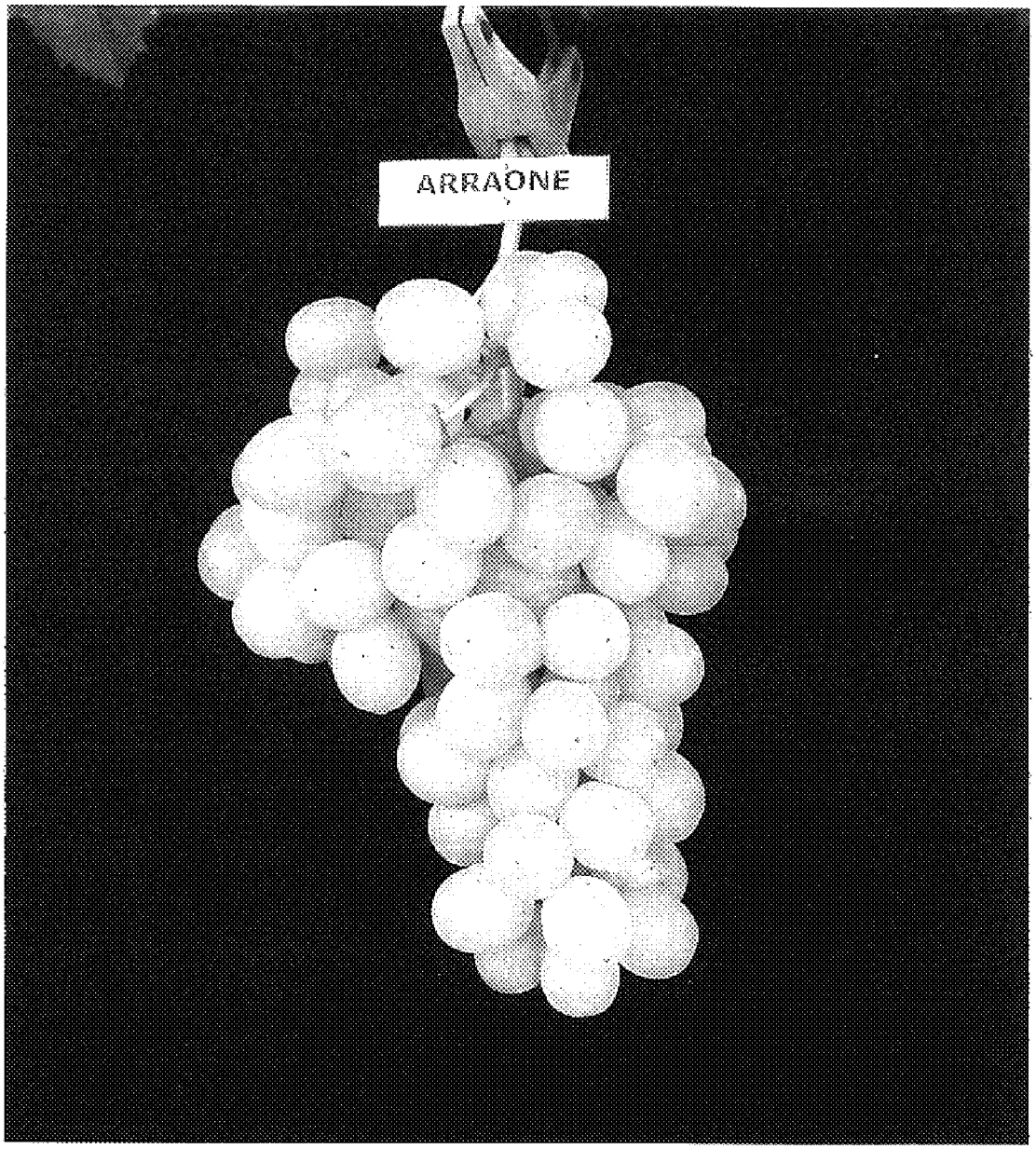
FIG. 2 shows a close-up of bunches of 'Arraone'.

Referring now specifically to the new and distinct variety of Grapevine, the following is a detailed description of 'Arraone' with color description where indicated by reference to The Royal Horticultural Society Colour Chart, except where common terms of color definition are employed.

The new variety of Grapevine as herein described may vary in slight detail due to climatic, soil and cultural conditions under which the variety may be grown, the present description being of four year old specimens of the variety as grown from its own root at Bakersfield, Calif., between April and September of 2003.

Plant characteristic:

*Form.*—Upright with an extremely long and large canopy.

*Growth.*—High, vigorous growth, with large canes and wide trunk.

Vegetative characteristics:

*Trunk.*—Size — medium developed for age, ranges from 1⅞ to 2.0 inches, measured within a few inches from the base of the trunk. Surface texture — rough with a fibrous, shaggy exterior. Color — light maple brown (Greyed-orange 177/B with darker strips of 187/A).

*Young shoot.*—Form of tip — Fully open. Anthocyanin coloration of tip — Medium. Density of prostrate hairs on tip — Medium. Density of erect hairs on tip — Very sparse. Color of dorsal side of internode (Well illuminated) — Green and red striped (Yellow green near 146C, Red purple near 59B). Color of ventral side of internode (Without direct sunlight) — completely green (Yellow green near 146C).

*Mature shoot.*—Attitude (habit) — Erect. Color of dorsal side of internode (Well illuminated) — (Dormant shoot color): Greyed orange near 166C with burgundy red strips (Greyed orange group near 177A). Color of ventral side of internode (Without direct sunlight) — (Dormant shoot color): Greyed Orange Group near 166D with burgundy red strips (Greyed Orange Group near 177B). Color of dorsal side of node (Well illuminated) — Green and red striped (Yellow green group near 146C). Color ventral side of node (without direct sunlight) — completely green, (Yellow green group near 146C). Density of erect hairs on node — Medium. Erect hairs on internode — Present. Density of prostrate hairs on node — Medium. Density of prostrate hairs on internode — Medium. Number of consecutive tendrils — Three or more. Length of tendrils — Very short, about 8¾ cm.

*Young leaf.*—Color of upper surface (recorded on the first 4 distal unfolded leaves — Green (Yellow green group near 146C). Density of prostrate hairs between veins (Recorded on the lower surface of the $4^{th}$ distal unfolded leaf) — Very sparse. Density of erect hairs between veins (recorded on the lower surface of the $4^{th}$ distal unfolded leaf) — Dense. Density of prostrate hairs on main veins (recorded on the lower surface of the $4^{th}$ distal leaf) — Very sparse. Density of erect hairs on main veins (recorded on the lower surface of the $4^{th}$ distal leaf) — Dense.

*Mature leaf.*—Size of (Recorded on mature leaves above the cluster within the medium third of shoot) — Medium. Shape of blade — Wedge-shaped. Number of lobes — five leaf lobes. Size of leaf: length about 1¾ inches, width about 1¾ inches. Top color — Green group near 137B. Bottom color — Green group near 137C. Petiole color — Greyed red group near 178A. Anthocyanin coloration on main veins on upper side of blade (Recorded on leaves above the cluster at the medium third of shoot) — Absent. Profile (cross-section at the middle of the leaf blade) — V-shaped. Blistering of blade upper surface — Absent. Shape of teeth (Recorded on the lateral lobe) — Both sides straight (rectilinear). Length of teeth: Medium. Ratio length/width of teeth — Large. General shape of petiole sinus (Degree of the opening of the petiole sinus) — Wide open. Tooth of petiole sinus — Present. Petiole sinus limited by veins — Absent. Shape of upper lateral sinus (Degree of the opening of the upper lateral sinus). A sinus results from a clear interruption of teeth on the leaf margin. The upper lateral sinus is situated between the middle vein and next lateral main vein — open. Depth of upper lateral sinus — Medium, about ½ inch. Density of prostrate hairs between veins (recorded on the lower side of blade) — Very sparse. Density of erect hairs between veins (Recorded on the lower side of blade) — Dense. Density of prostrate hairs on main veins (Recorded on the lower side of blade) — Very sparse. Density of erect hairs on main veins (Recorded on the lower side of blade) — Very sparse. Density of prostrate hairs on main veins (Recorded on the upper surface of the blade) — Present. Length petiole compared to middle vein — average length ⅛ inch.

*Woody shoot.*—Surface — Smooth. Main color — Greyed orange group near 166C with reddish brown stripes (Greyed orange group near 166A).

Inflorescence and fruit:

*Inflorescence.*—Sex of flower — Male and Female fully developed.

*Flower.*—Length of pistil — ⅛ inch. Color of pistil — light yellow green (Yellow green group near 149D). Length of stamen — ⅛ inch. Color of stamen — Yellow-green group near 148B.

*Bunch.*—Size (without peduncle) — Large, length about 7½ inches, width about 6¾ inches. Density — Medium (densely distributed berries, pedicles not visible). Length of peduncle (Measured in centimeters from insertion to first ramification) — average length ⅛ inch. Shape — short conical. Number of berries — approximately 125 to 135 berries per bunch. Average weight — 1 to 1½ pounds on untreated bunches. Color of penduncle — light yellow green (Yellow green near group 144D).

*Berry.*—Size — Large, Berry weight about 8.6 grams (untreated). Shape — Round. Presence of seed — Seed about 0.067×0.28 inches, berry width about 15/16 inches. Skin color (without bloom) light-dependent, recorded on berries which are exposed directly to sun — Green-yellow (Yellow green group near 151D). Skin bloom — weak. Skin texture — none bloom, smooth, medium thick skin. Weight — 10 berries, about 86 g. (berry weight, about 8.6 g.). Anthocyanin coloration of flesh — Colored, Yellow green 148B. Color of flesh — Yellow green group 148B. Juiciness of flesh — Very juicy. Firmness of flesh (Weight necessary for cracking the berries) — Medium. Tenacity of flesh — meaty solid flesh. Particular flavor — None. Ease of detachment from pedicel — Slightly easy.

*Seed.*—Length — Short. 100-seed weight — Very low. Transversal ridges on side — Absent.

Plant descriptors: All information below based on growing the variety in the Southern part of California.

*Time of bud burst (only varieties for fruit production).*—During the 3rd week of February.

*Inflorescence (number of inflorescence per shoot).*—Mostly two, seldom one.

*Time of berry ripening (veraison).*—Berry ripening in the middle of August.

*Bunch length (without peduncle).*—Bunch length varies from about 5½ inches to about 7½ inches.

*Berry thickness of skin (thickness of epidermis plus hypodermis).*—Medium skin thickness, about 175 μm.

*Market use information.*—Shipping quality of the fruit is very good both in storage and transportation. The fruit also has an excellent keeping quality, including excellent shelf life, and attractive appearance on shelf for extend periods.

*Resistance/susceptibility to disease and pest.*—No difference from other *Vitis Vinifera* varieties.

Comparison to Thompson seedless: Thompson seedless berry shape and color is the closest commercial common variety to the new variety, 'Arraone'. The harvest time of Thompson seedless is close as well, the new variety maturity time is about 30 days later than Thompson seedless, the vine size of the new variety is smaller by 20% than Thompson seedless.

The Thompson seedless leaves are different from the new variety by their thickness, the Thompson seedless leaves being much thinner than the new variety. The 'Arraone' variety sinus is about 2⅛ inches in depth while the Thompson seedless sinus is about 1½ inches.

*Thompson seedless leaf color.*—Upper side is Green group near color 137A; Bottom side is Green group near color 137C.

Leaves of the same age are almost equivalent in size. The leaf of the Thompson seedless variety (about 8½ inches) is slightly wider than that of the 'Arraone' variety (from about 3 5/16 inch to about 4 3/16 inch).

The canes are smooth and round in both varieties, however the cane color of the Thompson seedless is brighter than that of the new variety.

*Cluster and berries shape.*—Fruit shape — Thompson Seedless variety have elongate berry with long bunches and low-medium fertility while the new variety berry is round and large. Fruit set — both varieties are self fertile and set high number of berries.

The common characteristics of the two varieties is very small and in fact they are different in most aspects, but unfortunately there is no other white variety of the close period of ripening.

We claim:

1. A new and distinct variety of grapevine, botanically known as *Vitis* sp., identified as 'Arraone', substantially as shown and described herein.

* * * * *